(12) United States Patent
Van Ingelgem et al.

(10) Patent No.: US 8,864,732 B2
(45) Date of Patent: *Oct. 21, 2014

(54) TAMPON

(75) Inventors: Werner Van Ingelgem, Zele (BE); Annick De Poorter, Zele (BE); Steven Smet, Zele (BE)

(73) Assignee: Ontex Hygieneartikel Deutschland GmbH, Grosspostwitz (DE)

( * ) Notice: Subject to any disclaimer, the term of this patent is extended or adjusted under 35 U.S.C. 154(b) by 939 days.

This patent is subject to a terminal disclaimer.

(21) Appl. No.: 11/813,970

(22) PCT Filed: Jan. 18, 2006

(86) PCT No.: PCT/EP2006/000407
§ 371 (c)(1),
(2), (4) Date: Feb. 8, 2008

(87) PCT Pub. No.: WO2006/077091
PCT Pub. Date: Jul. 27, 2006

(65) Prior Publication Data
US 2008/0200892 A1    Aug. 21, 2008

(30) Foreign Application Priority Data
Jan. 19, 2005   (EP) ..................... 05447004

(51) Int. Cl.
*A61F 13/20*    (2006.01)

(52) U.S. Cl.
CPC ......... *A61F 13/2051* (2013.01); *A61F 13/2091* (2013.01); *A61F 13/2034* (2013.01); *Y10S 604/904* (2013.01)
USPC ...................... 604/385.18; 604/380; 604/904

(58) Field of Classification Search
CPC . A61F 13/20; A61F 13/2083; A61F 13/2085; A61F 13/2091; A61F 13/2097
USPC ............. 604/385.18, 904, 379, 380; D24/125
See application file for complete search history.

(56) References Cited

U.S. PATENT DOCUMENTS

| 435,491 A | 9/1890 | Fredigke |
| 1,731,665 A | 10/1929 | Huebsch |

(Continued)

FOREIGN PATENT DOCUMENTS

| AU | 2006263937 | 1/2007 |
| DE | 3 934 153 | 4/1991 |

(Continued)

OTHER PUBLICATIONS

International Search Report dated Apr. 11, 2006.

(Continued)

*Primary Examiner* — Lynne Anderson
(74) *Attorney, Agent, or Firm* — Knobbe, Martens, Olson & Bear LLP

(57) ABSTRACT

A tampon suitable for feminine hygiene and/or medical purposes having a longitudinal body provided with a dome-shaped insertion end and a withdrawal end, from which a withdrawal cord extends is disclosed. The tampon is made of compressed absorbent fibrous material and has an outer circumferential surface which is at least partially provided with longitudinal grooves that are separated from each other by longitudinal ribs. The path of the grooves and the ribs in the longitudinal direction of the tampon correspond to a continuous curved line that has only one point of inflection defining one convex part and one concave part, and that preferably does not show a maximum and/or a minimum.

23 Claims, 5 Drawing Sheets

(56) References Cited

U.S. PATENT DOCUMENTS

| | | |
|---|---|---|
| 1,941,717 A | 1/1934 | Rabell |
| 1,964,911 A | 7/1934 | Haas |
| 2,263,909 A | 11/1941 | Webb |
| 2,355,628 A | 8/1944 | Calhoun |
| 2,425,004 A | 8/1947 | Rabell |
| 2,444,528 A | 7/1948 | Popper et al. |
| 2,499,414 A | 3/1950 | Rabell |
| 2,652,056 A | 9/1953 | Lay |
| 2,706,986 A | 4/1955 | Carrier |
| 2,798,260 A | 7/1957 | Niepmann et al. |
| 2,965,101 A | 12/1960 | Schirmer et al. |
| 3,011,495 A | 12/1961 | Brecht |
| 3,013,558 A | 12/1961 | Leupold |
| 3,101,713 A | 8/1963 | Sargent |
| 3,138,159 A | 6/1964 | Schmidt |
| 3,148,680 A | 9/1964 | Roberts et al. |
| 3,196,873 A | 7/1965 | Beltzinger et al. |
| 3,397,695 A | 8/1968 | Voss |
| 3,431,909 A | 3/1969 | Krusko |
| 3,610,243 A | 10/1971 | Jones, Sr. |
| 3,643,661 A | 2/1972 | Crockford |
| 3,696,812 A | 10/1972 | Jaycox |
| 3,717,149 A | 2/1973 | Morane |
| 3,834,389 A | 9/1974 | Dulle |
| 3,981,305 A | 9/1976 | Ring |
| 4,077,409 A | 3/1978 | Murray et al. |
| 4,109,354 A | 8/1978 | Ronc |
| 4,175,561 A | 11/1979 | Hirschman |
| 4,276,881 A | 7/1981 | Lilaonitkul |
| 4,291,696 A | 9/1981 | Ring |
| 4,294,253 A | 10/1981 | Friese |
| 4,305,391 A | 12/1981 | Jackson |
| 4,328,804 A | 5/1982 | Shimatani |
| 4,361,151 A | 11/1982 | Fitzgerald |
| 4,405,323 A | 9/1983 | Auerbach |
| 4,479,791 A | 10/1984 | Sprague |
| 4,676,773 A | 6/1987 | Sheldon |
| 4,726,805 A | 2/1988 | Sanders, III |
| 4,755,166 A | 7/1988 | Olmstead |
| 4,787,895 A | 11/1988 | Stokes et al. |
| 4,816,100 A | 3/1989 | Friese |
| 4,891,042 A | 1/1990 | Melvin et al. |
| 4,911,687 A | 3/1990 | Stewart et al. |
| 4,960,417 A | 10/1990 | Tarr et al. |
| 5,165,152 A | 11/1992 | Kramer et al. |
| 5,330,421 A | 7/1994 | Tarr et al. |
| 5,346,468 A | 9/1994 | Campion et al. |
| 5,374,258 A | 12/1994 | Lloyd et al. |
| 5,403,300 A | 4/1995 | Howarth |
| 5,445,605 A | 8/1995 | Pluss |
| 5,531,674 A | 7/1996 | Frayman |
| 5,542,914 A | 8/1996 | Van Iten |
| 5,592,725 A * | 1/1997 | Brinker ............... 28/118 |
| 5,895,408 A | 4/1999 | Pagan |
| 5,909,884 A | 6/1999 | Schwankhart |
| 5,911,712 A * | 6/1999 | Leutwyler et al. ........... 604/379 |
| 6,177,608 B1 | 1/2001 | Weinstrauch |
| 6,206,867 B1 | 3/2001 | Osborn et al. |
| 6,310,269 B1 * | 10/2001 | Friese et al. ............. 604/379 |
| 6,358,235 B1 | 3/2002 | Osborn et al. |
| 6,433,246 B1 | 8/2002 | Nguyen et al. |
| 6,478,786 B1 | 11/2002 | Glaug et al. |
| D485,354 S * | 1/2004 | Carlin et al. ............. D24/125 |
| 6,719,743 B1 | 4/2004 | Wada |
| 6,748,634 B2 | 6/2004 | Nguyen et al. |
| 6,755,808 B2 | 6/2004 | Balogh et al. |
| 6,889,409 B2 | 5/2005 | Friese et al. |
| 6,939,340 B1 * | 9/2005 | Berges ................. 604/385.17 |
| 6,953,456 B2 | 10/2005 | Fuchs et al. |
| 7,059,026 B2 | 6/2006 | Friese et al. |
| 7,070,585 B2 * | 7/2006 | Jensen ................. 604/385.17 |
| 7,087,045 B2 | 8/2006 | Jensen |
| 7,338,483 B2 * | 3/2008 | Carlin et al. ............. 604/385.17 |
| 7,967,803 B2 | 6/2011 | Van Ingelgem et al. |
| 2001/0014348 A1 | 8/2001 | Schoelling |
| 2002/0151859 A1 | 10/2002 | Schoelling |
| 2002/0157222 A1 | 10/2002 | Friese et al. |
| 2003/0097108 A1 | 5/2003 | Hasse et al. |
| 2003/0176844 A1 | 9/2003 | Randall et al. |
| 2003/0208180 A1 | 11/2003 | Fuchs et al. |
| 2004/0030316 A1 | 2/2004 | Gubernick et al. |
| 2004/0199137 A1 | 10/2004 | Lamb |
| 2005/0055001 A1 | 3/2005 | Cazzato et al. |
| 2005/0113780 A1 | 5/2005 | Gatto et al. |
| 2005/0113783 A1 | 5/2005 | Carlin et al. |
| 2005/0113787 A1 | 5/2005 | Carlin |
| 2005/0113788 A1 * | 5/2005 | Carlin ................. 604/385.18 |
| 2005/0113789 A1 | 5/2005 | Jensen |
| 2005/0113807 A1 | 5/2005 | Carlin |
| 2005/0143708 A1 | 6/2005 | Hagberg et al. |
| 2005/0177090 A1 | 8/2005 | Jensen |
| 2005/0193536 A1 | 9/2005 | Ingelgem et al. |
| 2005/0256511 A1 | 11/2005 | Chase et al. |
| 2005/0277904 A1 | 12/2005 | Chase et al. |
| 2005/0283128 A1 | 12/2005 | Chase et al. |
| 2006/0111662 A1 | 5/2006 | Karapasha et al. |
| 2006/0167429 A1 | 7/2006 | Denti et al. |
| 2006/0167430 A1 | 7/2006 | Denti et al. |
| 2006/0241556 A1 | 10/2006 | Lochte et al. |
| 2007/0083182 A1 | 4/2007 | Schoelling |
| 2008/0154176 A1 | 6/2008 | Van Ingelgem et al. |
| 2008/0195029 A1 | 8/2008 | Van Ingelem et al. |
| 2008/0200892 A1 | 8/2008 | Van Ingelgem et al. |
| 2008/0221502 A1 | 9/2008 | Binner et al. |
| 2009/0024103 A1 * | 1/2009 | Van Ingelgem et al. ...... 604/379 |
| 2009/0082712 A1 | 3/2009 | Hasse |
| 2010/0121251 A1 | 5/2010 | Van Ingelgem et al. |
| 2010/0318053 A1 | 12/2010 | Smet |
| 2011/0201992 A1 | 8/2011 | Smet et al. |
| 2011/0230854 A1 | 9/2011 | Smet |
| 2011/0238028 A1 | 9/2011 | Smet |
| 2012/0010587 A1 | 1/2012 | Smet |
| 2012/0089111 A1 | 4/2012 | Magnusson et al. |

FOREIGN PATENT DOCUMENTS

| | | |
|---|---|---|
| DE | 4 304 505 | 8/1994 |
| DE | 4 325 220 | 2/1995 |
| DE | 103 06 678 | 8/2004 |
| DE | 20320992 | 8/2005 |
| DE | 10 2005 030 182 | 1/2007 |
| DE | 10 2005 05051 | 4/2007 |
| EP | 0355 396 | 2/1990 |
| EP | 0 422 660 | 4/1991 |
| EP | 0 639 363 | 2/1995 |
| EP | 0 692 233 | 1/1996 |
| EP | 1 027 874 | 8/2000 |
| EP | 1 108 408 | 6/2001 |
| EP | 1 208 827 | 5/2002 |
| EP | 1 459 720 | 9/2004 |
| EP | 1 481 656 | 12/2004 |
| EP | 1498093 | 1/2005 |
| EP | 1 547 554 | 6/2005 |
| EP | 1 547 555 | 6/2005 |
| EP | 1683503 | 7/2006 |
| EP | 1 695 680 | 8/2006 |
| EP | 1704841 | 9/2006 |
| GB | 2120945 | 12/1983 |
| WO | WO 91/06272 | 5/1991 |
| WO | WO 96/27353 | 9/1996 |
| WO | WO 00/53141 | 9/2000 |
| WO | WO 02/49686 | 6/2002 |
| WO | WO 02/076357 | 10/2002 |
| WO | WO 02/078586 | 10/2002 |
| WO | WO 2005/063162 | 7/2005 |
| WO | WO 2007/088057 | 8/2007 |
| WO | WO 2009/129910 | 10/2009 |
| WO | WO 2011/002357 A1 | 1/2011 |

OTHER PUBLICATIONS

Search Report dated Jun. 4, 2004 from European Patent Application No. 03447303.

(56) References Cited

OTHER PUBLICATIONS

Search Report dated Apr. 11, 2006 from International Patent Application No. PCT/EP2006/000407.
Partial Search Report dated Aug. 17, 2005 from European Patent Application No. 05447004.
Search Report dated Nov. 10, 2005 from European Patent Application No. 05447065.
Search Report dated Apr. 28, 2006 from International Patent Application No. PCT/EP2006/001598.
Partial Search Report dated Nov. 14, 2005 from European Patent Application No. 05447042.
Search Report dated Jun. 29, 2007 from International Patent Application No. PCT/EP2007/000872.
Search Report dated Jun. 5, 2008 from International Patent Application No. PCT/EP2008/051418.
Office Action dated Jan. 23, 2007 from U.S. Appl. No. 11/021,671, filed Dec. 22, 2004.
Office Action dated Jul. 11, 2007 from U.S. Appl. No. 11/021,671, filed Dec. 22, 2004.
Office Action dated Mar. 6, 2008 from U.S. Appl. No. 11/021,671, filed Dec. 22, 2004.
Office Action dated Nov. 28, 2008 from U.S. Appl. No. 11/021,671, filed Dec. 22, 2004.
Office Action dated Jun. 24, 2009 from U.S. Appl. No. 11/021,671, filed Dec. 22, 2004.
Office Action dated Mar. 18, 2010 from U.S. Appl. No. 11/021,671, filed Dec. 22, 2004.
Office Action dated Sep. 21, 2009 from U.S. Appl. No. 11/909,250, filed Sep. 20, 2007.
Office Action dated Apr. 16, 2010 from U.S. Appl. No. 11/909,250, filed Sep. 20, 2007.
Office Action dated Sep. 30, 2009 from U.S. Appl. No. 11/816,908, filed Aug. 22, 2007.
Office Action dated May 13, 2010 from U.S. Appl. No. 11/816,908, filed Aug. 22, 2007.
Office Action dated Sep. 22, 2010 from U.S. Appl. No. 12/278,228, filed Aug. 4, 2008.
Final Office Action for U.S. Appl. No. 12/278,228 dated Mar. 22, 2011.
International Search Report for International application No. PCT/EP2009/067047, dated Feb. 17, 2010 by European Patent Office.
International Search Report for International application No. PCT/EP2009/065089, dated Jun. 9, 2010 by European Patent Office.
International Search Report for International application No. PCT/EP2009/063998, dated Mar. 11, 2010 by European Patent Office.
European Search Report dated Jan. 20, 2011 from European patent Application No. EP10169007.1.
International Search Report for International Application No. PCT/US2005/017884, mailed on Apr. 28, 2006.
International Search Report for International Application No. PCT/EP2011/061435, mailed on Aug. 9, 2011.
International Search Report for International Application No. PCT/EP2006/002075, mailed on Jun. 7, 2006.
Office Action dated Oct. 13, 2011 from U.S. Appl. No. 11/816,908, filed Aug. 22, 2007.

* cited by examiner

TAMPON

RELATED APPLICATIONS

This application is the U.S. National Phase under 35 U.S.C. §371 of International Application PCT/EP2006/000407, filed Jan. 18, 2006, which claims priority to EP 05447004.2, filed Jan. 19, 2005.

FIELD OF THE INVENTION

The present invention relates to a tampon suitable for feminine hygiene and/or medical purposes.

BACKGROUND

Intravaginal tampons are in common use by women for the retention of fluids or menses discharged along the walls of the vagina during the menstrual cycle. The menstrual discharge, comprising endometrial cells, secretions and blood, is intermittent and takes place over hours and days. The blood and other matter exude following the line of gravity. Sometimes the flow is light, sometimes heavy. Intravaginal tampons are usually formed of absorbent materials such as cotton, rayon cellulose wading, synthetic sponge, cellulose fluff, synthetic fibres or combinations of these materials and compressed or moulded usually to a generally cylindrical configuration of a size to fit within the vaginal tract.

Tampons having an insertion end, a withdrawal end, a withdrawal cord and a central section extending therebetween are well known in the art. From the prior art, cylindrical shaped tampons are known having ribs defined by grooves, said ribs extending radially outwards. Such tampons are known for example from WO 02/078586, EP 0 422 660, US 2002/0157222, U.S. Pat. Nos. 5,592,725, 5,895,408, EP 1 108 408, US 2003/0208180, WO 00/53141 and EP 0 639 363.

Tampons with grooves in the longitudinal direction of the tampon are known in the art.

For instance, WO 02/078586 and WO 02/076357 disclose tampons having spirally shaped grooves. The outer surface of the tampons provided with spirally shaped, pressed longitudinal grooves describing a straight path in the longitudinal direction of said tampon. However, a disadvantage of such spirally-grooved tampon is that its absorption of fluid is generally insufficient and relatively slow, such that by-pass and leakage problems may occur after the tampon has been put into use.

EP 1 459 720 describes a vaginal tampon having sinusoidal grooves along the outer surface, separated by longitudinal ribs. The grooves and ribs in these tampons follow an undulating path in the longitudinal direction of the tampon, which shows a periodic pattern. More in particular, the grooves and ribs follow an undulating path, with alternating larger and smaller curvatures.

Grooved tampons are generally manufactured by bringing fibrous material between press jaws. In the prior art, pressing machines are known to have penetrating segments, which form ribs defined by grooves and which penetrate the absorbing material in essentially a radial direction, i.e. in a direction leading to the central axis of the tampon. As a result, the ribs extend radially outwards and their medians form an essentially straight line towards the central axis of the tampon. Such machines are known for example from EP 0 422 660 and EP 0 639 363.

A grooved tampon can be formed with the following steps: rolling up a length of a continuous fibrous web to form a generally cylindrical tampon blank with a circumferential surface; simultaneous radial pressing of narrow, strip-shaped sections of the circumferential surface of the tampon blank arranged in a spaced manner to form a number of longitudinal grooves which are separated from one another by relatively uncompressed longitudinal ribs which extend radially outwards from a relatively compressed core, the core being compressed to a smaller extent in the area of the recovery end of the tampon than in its remaining area; and pressing of outer ends of the longitudinal ribs radially inwards to form a soft, smooth circumferential surface, while the relatively uncompressed fibrous structure of the ribs is preserved.

However, a problem associated with the above-described tampons having sinusoidally-shaped grooves in the longitudinal direction is that their process of manufacture is complicated, showing a low efficacy, and involving considerable material loss. More in particular, a problem can occur during insertion and/or withdrawal of a tampon in and/or out of the pressing apparatus. Friction can occur between the tampon grooves and the pressing apparatus. Elements of the pressing apparatus may obstruct the tampon in its path out of the pressing apparatus. As a consequence thereof sinusoidally-shaped tampons grooves can at least partly be destroyed when taking the compressed tampons out of the pressing apparatus. Tampons with partly destroyed ribs and grooves are of lower quality, can not be commercialized and have to be thrown away. This implicates a substantial loss of material, inefficiency of the production system and considerable increase in production costs of the tampons. In addition, obstruction during insertion and/or withdrawal of the tampon out of the pressing apparatus is disadvantageous in view of rapid and mass production of these tampon products.

In view hereof, it is clear that there is a need in the art for a tampon, which overcomes one ore more of these problems of the prior art. More in particular, there is a need in the art for a tampon of which the manufacture process is improved. There is also a need in the art for a tampon having improved absorption capacity compared to spirally-grooved tampons known in the prior art.

It is therefore an object of the invention to provide a tampon with an improved configuration, which is easier and more cost effective to fabricate. More in particular, it is an object of the invention to provide a tampon, which can be easily retracted out of a pressing apparatus without substantially destroying the formed grooves and ribs of the tampon.

It is further an aim of the invention to provide a tampon of which the grooves and ribs do not describe a straight or periodic path in the longitudinal direction of the tampon.

The present invention further aims to provide a tampon having improved absorption capacity compared to spirally-grooved tampons known in the prior art.

It is further an aim of the invention to provide a tampon that is soft to the touch and therefore comfortable to insert into the body cavity.

The advantages of the present tampons will become clear to the persons skilled in the art from the description and the accompanying figures provided below.

SUMMARY

The present invention relates to a tampon in particular for feminine hygiene having a longitudinal body showing in compressed condition a length L in the axial direction of the tampon body and a width W in the transversal direction of the tampon body, whereby said tampon essentially consists of compressed absorbent fibrous material and has an outer circumferential surface which is at least partially provided with longitudinal grooves that are separated from each other by longitudinal ribs. The longitudinal body is essentially of a cylindrical shape.

The tampon is in particular characterized in that the path of said grooves and said ribs in the longitudinal direction of said tampon corresponds to a continuous curved line having only one point of inflection defining one convex part and one concave part.

The term "continuous" as used herein refers to a curve or function, which extends without break or irregularity.

As used herein, the term "convex part", refers to a part of a curve that curves or bulges outward. The convex part may be open or closed. An "open convex pad" refers to a curve which does not include a point wherein the first derivative is zero. A point wherein the first derivative is zero corresponds to a maximum or a minimum in the curve. In this case the convex part of the curve may approach an asymptote which is parallel to the longitudinal path of the curve, and the maximum or minimum may be present at infinity. A "closed convex part" refers to a curve which includes only one point wherein the first derivative is zero.

As used herein, the term "concave part", refers to a part of a curve that curves inward. The concave part may be open or closed. An "open concave part" refers to a curve which does not include a point wherein the first derivative is zero. A point wherein the first derivative is zero corresponds to a maximum or a minimum in the curve. In this case the concave part of the curve may approach an asymptote which is parallel to the longitudinal path of the curve, and the maximum or minimum may be present at infinity. A "closed concave part" refers to a curve which includes only one point wherein the first derivative is zero.

The term "point of inflection" refers to the point on a curve where the curvature of the curve changes; and in particular to a point where the curve changes from a convex to a concave curves or to a convex part of a curve to a concave part of a curve, or vice versa. Such point is in particular characterized in that the second derivative thereof is zero.

In a particularly preferred embodiment, the tampon is in particular characterized in that the path of said grooves and said ribs in the longitudinal direction of said tampon corresponds to the function $$y = a\, x^m$$

wherein m is an odd positive whole number which is different from 1,
wherein a is different from zero,
wherein y corresponds to a value in the axial direction Y of the tampon body, and
wherein x corresponds to a value in the transversal direction X of the tampon body.

In another particularly preferred embodiment, the path of said grooves and said ribs in the longitudinal direction of said tampon corresponds to a hyperbolic function or an inverse hyperbolic function.

The present tampons have an outer circumferential surface which is provided with longitudinal grooves and ribs that show an optimally curved path in the direction of the tampon body, such that the obtained grooves show an optimal length and curvature.

The present configuration of the grooves gives the present tampon several important advantages.

On one hand, the grooves in the present tampons are substantially longer than grooves which follow an essentially straight path in the longitudinal direction, such as spirally-grooved tampons. Longer grooves as present in the present tampons substantially improve the tampons' absorptive capacity. The groove configuration of the present tampon thus gives substantially more expansion and absorption capacity to the tampon, compared to tampons having grooves that follow an essentially straight path.

On the other hand, the present tampons do not show the problems of tampons having periodical sinusoidal grooves, the latter grooves being too long to provide sufficient continuity to the grooves. Tampons showing sinusoidal grooves cannot be retracted out of a pressing apparatus without undergoing considerable friction which could at least partly destroy the formed grooves, as explained above. Such grooves follow a periodic path in the longitudinal direction of the tampon body that shows more than one point of inflection. There is thus more than one point where the direction of the groove path changes in the longitudinal direction of the tampon body. The path of such grooves thus shows several points where friction may occur with elements of a pressing apparatus, which greatly complicates their efficient fabrication process.

The present invention provides tampons having an improved configuration, which permits facilitated and more effective production of the tampon. More in particular, due to the particular configuration of the tampon, during manufacture, and more precisely when taking the tampons out of the pressing apparatus, grooves and ribs are not again partly destroyed. At the end of the pressing operation, the tampon is normally withdrawn out of the pressing apparatus in a longitudinal direction. The penetrating segments of the press jaws are normally not completely raised out of the tampon grooves during this withdrawal action. However, in the present configuration, the penetrating segments do not substantially hinder or obstruct withdrawal of the tampons. Withdrawal of the finished tampon is essentially done in a straight line. Because the present tampons show grooves that follow a path that is essentially in line with the longitudinal withdrawal direction and only shows one point of inflection, friction between the tampon grooves and the pressing apparatus can be considerably minimized. Advantageously, the production process for preparing tampons is thus more efficient in terms of time and the loss of material can be significantly reduced.

In another aspect, the invention relates to a method for producing a tampon, comprising the steps of:
 providing a tampon blank of fibrous material having a longitudinal axis;
 compressing in a press the tampon blank and forming longitudinal grooves at an outer circumferential surface of the tampon which follow the path in the longitudinal direction of said tampon of a continuous curved line having one point of inflection defining one convex part and one concave part, and
 withdrawing said pressed tampon out of the press in a longitudinal direction of the tampon body.

In yet another embodiment, the invention relates to a press suitable for manufacturing of a tampon according to the invention by pressing absorbing material radially, and comprising press jaws including penetrating segments for pressing the absorbing material radially and pressing shoulders.

Those skilled in the art will immediately recognise the many advantages of the present invention from the detailed description and accompanying figures provided below.

DETAILED DESCRIPTION OF THE INVENTION

Figure 1:
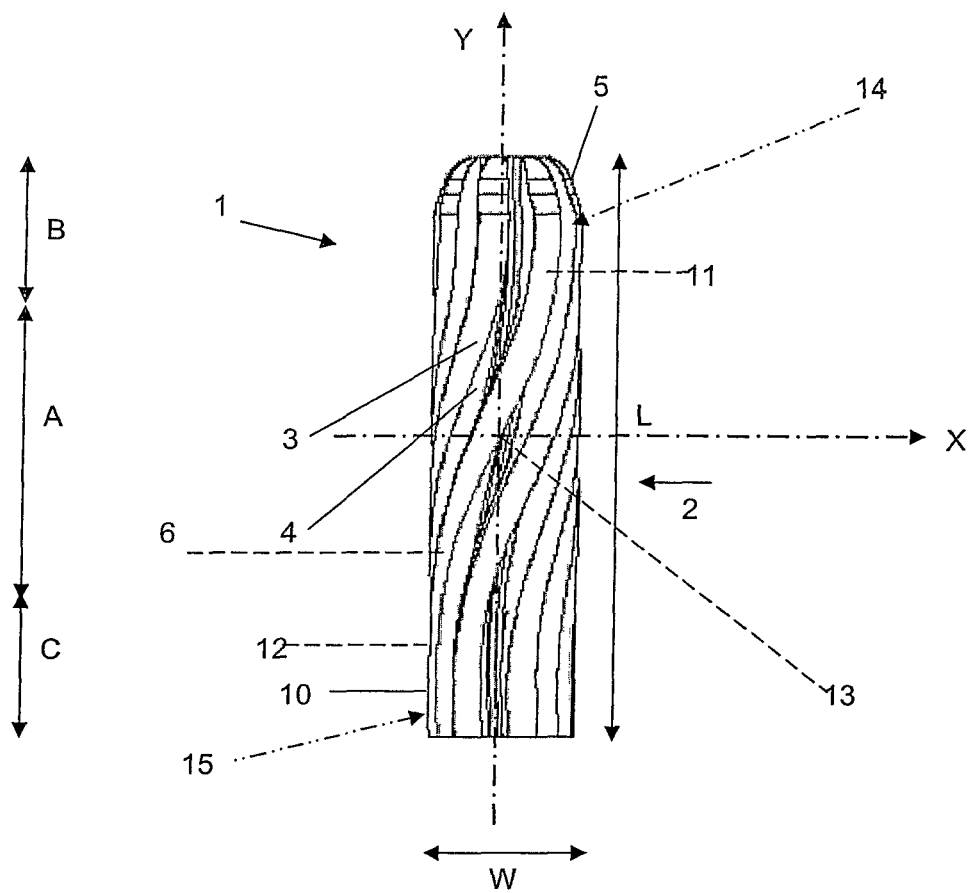
FIGS. 1 and 2 are schematic illustrations of embodiments of a tampon according to the invention. In the representations, the grooves and ribs are accentuated in order to better illustrate their curved path in the longitudinal direction of the tampon body FIG. 3 schematically represents the sinusoidal (periodic) path of grooves and ribs of a prior art tampon in the longitudinal (axial) direction Y of the tampon.

The present invention relates to a tampon suitable for feminine hygiene and medical purpose having a longitudinal body in an essentially cylindrical shape. The tampon may be provided with an insertion end and a withdrawal end.

In compressed condition, the tampon has a length L and a width W. In compressed condition the length of the tampon is indicated with L. The term "length of the tampon" refers to the length in axial direction Y of the tampon body. The term "width of the tampon" refers to the width of the tampon body in transversal direction X in compressed condition.

The tampon essentially consists of compressed absorbent fibrous material and has an outer circumferential surface which is at least partially provided with longitudinal ribs defined by longitudinal grooves. It is noted that the terms "absorbent fibrous material" and "absorbent fibers" are used herein as synonyms.

The present tampon is in particular characterized in that the path of the tampon grooves and tampon ribs in the longitudinal direction of the tampon corresponds to a continuous curved line, and preferably to a curved line showing a convex part which is separated from a concave part by a single point of inflection.

For definitions for "convex part", "concave part" and "point of inflection" reference is made to the summary section of this application.

In a preferred embodiment, said point of inflection is substantially located in the middle part of the tampon longitudinal body. Preferably point of inflection is located in an area covering the middle 50% of the tampon longitudinal body area. Even more preferred, this point of inflection is located about an imaginary transversal line on the tampon at length L/2. It is noted that it is of utmost importance in the present tampon configuration that only one point of inflection is provided in the path of the tampon grooves. Because there is only one point of inflection, the path of the grooves will undergo only one change in direction. As a consequence thereof, friction between the tampon grooves and the pressing apparatus can be considerably minimized.

In a preferred embodiment, the tampon is characterised in that the path of the tampon grooves and tampon ribs in the longitudinal direction of the tampon corresponds to a continuous curved line, which is point symmetric in relation to said point of inflection.

In a particularly preferred embodiment, the tampon is characterised in that the path of the tampon grooves and tampon ribs in the longitudinal direction of the tampon corresponds to a continuous curved line which does not show a point having a first derivative equal to zero. In other words, the curve describing path of the grooves and ribs in the longitudinal direction of the tampon body does not show a minimum and/or maximum.

The path of the tampon grooves and tampon ribs in the longitudinal direction of the tampon corresponds to a continuous curved line, which preferably does not show any points wherein a first derivative is equal to zero. However, in an alternative embodiment, the path of the grooves and tampon ribs in the longitudinal direction of the tampon may correspond to a curved line showing one or two points which have a first derivative equal to zero. A first such point may be located in an area covering the top 25% of the tampon longitudinal body area, and for instance be located in the insertion end of the tampon. A second such point may be located in an area covering the bottom 25% of the tampon longitudinal body area, and for instance be located in the withdrawal end on the tampon. In an embodiment, a tampon is provided, wherein said curved line shows only one point which has a first derivative equal to zero, whereby a first point is located in an area covering the top 25% or in an area covering the bottom 25% of the tampon longitudinal body area. In another embodiment, a tampon is provided tampon wherein said curved line shows maximally two points which has a first derivative equal to zero, whereby a first point is located in an area covering the top 25% and a second point is located in an area covering the bottom 25% of the tampon longitudinal body area. In yet another embodiment, a tampon is provided wherein said point wherein the first derivative equal to zero is located at the top of the tampon, i.e. at −½ ,L. and/or at the bottom of the tampon, i.e. at +½ L.

As further indicated below, the insertion end of the tampon may have undergone some deformation in order to have a dome shape or the like. It will be understood from the present invention that the above-indicated first point may be integrated into the dome-like deformation of the insertion end. Likewise, as further indicated below, the withdrawal end of the tampon may also have undergone some deformation, e.g. in order to have a constricted shape. It will be understood from the present invention that also in such case the above-indicated second point may be integrated into the deformation of the withdrawal end.

In a preferred embodiment, the path of the grooves and the ribs in the longitudinal direction of said tampon corresponds to a curved line showing the function $$y = a x^m$$

wherein m is an odd positive whole number which is different from 1,
wherein a is different from zero,
wherein y corresponds to a value in the axial direction Y of the tampon body, and
wherein x corresponds to a value in the transversal direction X of the tampon body.

The above-referred function is a power function wherein x and y are the variables that are to be related, parameters a and m describe the relationship. The parameter a moves the values for $x^m$, up or down as an increase or decrease, respectively. The parameter m, determines the function's rates of growth or decay. Preferably the parameter m is a positive and odd whole number, different from zero and one and for instance 3, 5, 7, 9, etc.. the parameter a is different from zero and may for instance be −6, −5, −4, −3, −2, −1, 1, 2, 3, 4, 5, 6, etc. The longitudinal grooves and ribs preferably extend over at least 25° to 80° of the tampons' circumference, and preferably over 30 to 45° of the tampons' circumference.

In a particularly preferred embodiment, the invention relates to a tampon having an outer circumferential surface that is provided with longitudinal ribs defined by longitudinal grooves, whereby said grooves and said ribs follow a path in the longitudinal direction of said tampon which corresponds to a curved line showing the function $y=x^3$.

In alternative preferred embodiment, the invention relates to a tampon having an outer circumferential surface that is provided with longitudinal ribs defined by longitudinal grooves, whereby said grooves and said ribs follow in the longitudinal direction of said tampon the path of a continuous hyperbolic function or to a continuous inverse hyperbolic. The term "continuous" as used herein refers to a curve or function, which extends without break or irregularity.

Figure 6A:
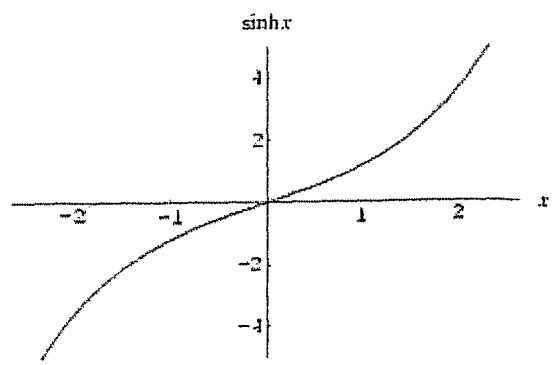
FIG. 6 A to C respectively represents a function corresponding to a hyperbolic sine of x, a hyperbolic tangent of x, and an inverse hyperbolic tangent of x.
Figure 6B:
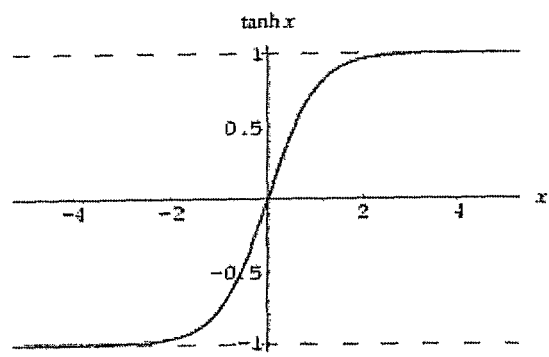

In a particularly preferred embodiment, the hyperbolic function corresponds to any of the following hyperbolic functions $y=\sin h (x)$ or $y=\tan h (x)$ wherein y corresponds to a value in the axial direction Y of the tampon body, and wherein x corresponds to a value in the transversal direction X of the tampon body. The function $y=\sin h(x)$ corresponds to a hyperbolic sine of x (see FIG. 6A), and can also be written as $y=\sin h(x)=(e^x-e^{-x})/2$. The function $y=\tan h(x)$ corresponds to a hyperbolic tangent of x (see FIG. 6B), and can also be written as $y=\sin h(x)/\cos h(x)$ whereby $\sin h(x)$ is $(e^x-e^{-x})/2$ and $\cos h(x)$ is $(e^x+e^{-x})/2$.

Figure 6C:
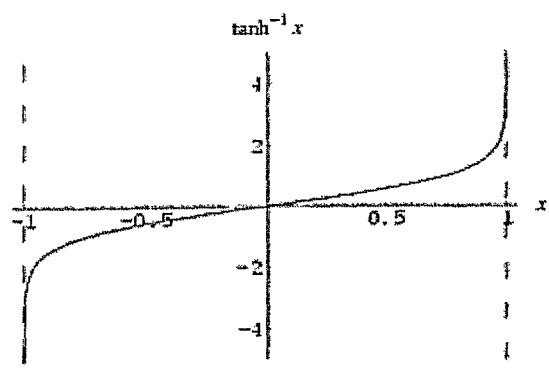

In a particularly preferred embodiment, the inverse hyperbolic function corresponds to the function $y=\operatorname{artan} h(x)$, wherein y corresponds to a value in the axial direction Y of the tampon body, and wherein x corresponds to a value in the transversal direction X of the tampon body. The function $y=\operatorname{artan} h(x)$ corresponds to inverse hyperbolic tangent of x (see FIG. 6C).

On a tampon according to the present invention an X,Y coordinate system can be represented, such that the Y axis divides the tampon in two halves in transversal direction and the X axis divides the tampon in two halves in axial direction (see also FIG. 1). In such case, the values for x and y in the above-indicated power or hyperbolic function may be as follows: x may be a value that is comprised between $+\frac{1}{2}W$ en $-\frac{1}{2}W$ and y may be a value that is comprised between $+\frac{1}{2}L$ and $-\frac{1}{2}L$.

The present tampons provide several important advantages.

The inventors have found that tampons comprising such grooves showing the herein defined path are easier and more time and cost effective to fabricate. The production of the tampon according to the invention is possible with tools (press jaws), which are able to radially press the fibrous material of the tampon blank. More in particular, the invention is in particular very suitable for being manufactured using a press apparatus showing press jaws with penetrating segments and/or cogs.

The present tampons are particularly suitable for being fabricated with the apparatus and according to the method as described in an European patent application of applicant having application number 03447303.3 and which was filed on Dec. 22, 2003 at the European Patent Office (and of which the publication number will be provided once available). The apparatus described in this patent application comprises a press for manufacturing a tampon by pressing the absorbing material radially comprising press jaws and pressing shoulders. The press apparatus is in particular characterized in that its press jaws show penetrating segments or cogs (tooth on the rim of the press jaws) for penetrating the absorbing material. The present tampon is in particular suitable for being manufactured using a press wherein press jaws show penetrating segments which essentially have a curved shape, and for instance the shape of a continuous curved line as defined herein. The tampons according to the present invention show a configuration which enables effective withdrawal of finished tampons out of a pressing apparatus without harming or at least partly destroying the grooves and ribs formed in the tampon. During withdrawal of the tampon out of the press, frictional contact between the grooves of the tampon and the penetrating segments can be considerably reduced.

Furthermore, such a tampon is softer and more comfortable to insert.

In addition, the inventors have found that tampons having grooves following the herein defined path show greater absorption and expansion prior to saturation and show increased expansion and absorption speed. The grooves of the tampons following the herein defined path are longer than straight-shaped or spirally-shaped grooves, and provide greater absorption. Furthermore, in the described configuration, the fibrous material which essentially determines the capacity of the tampon for absorbing the body fluid is better exploited. The present tampon provides good stretching (expansion) properties and shows improved sealing behavior, since during expansion the ribs and grooves of present tampon are capable of better fitting the shape and contours of the body cavity. Thus, the absorption capacities of the present tampons are certainly not impaired, but to the contrary may even be improved over prior art tampons not showing the present configuration.

In addition, grooves following the herein defined curved path permit a purposeful enlargement of the effective product surface. The grooves following the herein defined curved path enlarge the surface of the tampon and provide longer distances for the body fluid to traverse before leakage around the tampon occurs. This improvement can results from any depth of groove. However, it is preferred that the groove has a depth of at least about 1 mm, and preferably of more than about 4 mm, preferably about 4 mm to about 6 mm.

Absorbent fibrous material usable in the tampon according to the invention may consist of any absorbent material having acceptable absorbency and modulus of elasticity properties that is capable of absorbing and/or retaining liquid. The absorbent structure can be manufactured in a wide variety of sizes and shapes and from a wide variety of liquid-absorbing materials. It is, of course, desirable to use absorbent materials having a minimum content of extraneous soluble materials since the product may be retained in the body for a considerable period of time, i.e. absorbent materials contain no/little unnecessary soluble matter which could dissolve and enter the body. Retained soluble extraneous materials could cause a safety hazard if they are toxic, irritant, or sensitive. A representative, non-limiting list of useful materials includes cellulosic materials, such as rayon, cotton, wood pulp, creped cellulose wadding, tissue wraps and laminates, peat moss, and chemically stiffened, modified, or cross-linked cellulosic fibres; synthetic materials, such as polyester fibres, polyolefin fibres, absorbent foams, e.g. a flexible resilient polyurethane foam, absorbent sponges, super-absorbent polymers, absorbent gelling materials; formed fibres, such as capillary channel fibres and multi limbed fibres; synthetic fibres, or any equivalent material or combinations of materials, or mixtures of these.

Furthermore, the present invention relates to tampons, which can be applied digitally, as well as to tampons that can be applied with an applicator. An applicator used to position the tampon within the vagina can be any applicator known to those skilled in the art, e.g. the telescoping tube type applicator. The applicator can be made of any of the acceptable materials, e.g. cardboard or molded polyethylene. The applicator can be sized similarly to those presently commercially used.

The number of longitudinal ribs can vary, for example depending on the diameter of the tampon and/or the type of absorption material. Preferably, there are between 3 and 12 ribs, more preferably there are between 6 and 12 ribs and even more preferably, at least about 8. While the present invention, like many known tampons, may have an even number of ribs, it is also within the scope of the present invention to produce tampons with an odd number of ribs. Preferably, before use, the ribs fit closely together near the circumferential surface, providing an essentially cylindrical, smooth and soft surface. This facilitates handling of the tampon and makes insertion of the tampon more comfortable.

In an embodiment, the invention provides a tampon, wherein said tampon is at least partially surrounded by a covering. The covering is preferably not provided over the insertion end, in order to provide better access of the menses to the insertion end of the tampon. In order to improve the absorbing capacity and expansion capacity of the tampon, said covering is preferably a stretchable and/or elastic liquid-permeable covering. The covering can consist of, for example, a non woven covering material made of, for example, thermoplastic, heat sealing fibers or a plastic film. In another embodiment, the cover may also comprise a friction-lowering layer. Such a covering improves the comfort of introduction and prevents fibers from being detached during introduction or removal of the tampon into or from the body cavity.

A further preferred feature of the tampon of the invention is a withdrawal cord, extending from the withdrawal end of the tampon, in order to ease withdrawal of the tampon.

Also, the tampon is preferably provided with a round domed insertion end of high compression. This will make insertion of the tampon easier because the narrowed end goes deepest in the vagina.

A tampon may further be provided with a constricted withdrawal end. A "constricted withdrawal end", as used herein, refers to a withdrawal end which has a cross sectional diameter which is smaller than the cross-sectional diameter of the remaining tampon body. In a preferred embodiment, the invention provides a tampon, wherein said withdrawal end is a conical withdrawal end. The conical shape is one which is preferably truncated from its point. Such conical end guides the tampon during withdrawal, so making withdrawal easier. In another preferred embodiment, the invention provides a tampon, wherein said withdrawal end is a dome-shaped withdrawal end. In yet another embodiment the tampon according to the invention has a frusto-conical shape which considerably facilitates withdrawal of the tampon, especially when the tampon is not saturated.

In a further preferred embodiment, the withdrawal end is provided with a finger recess according to any technique known in the art. This facilitates the handling and the insertion of the tampon.

Figure 2:
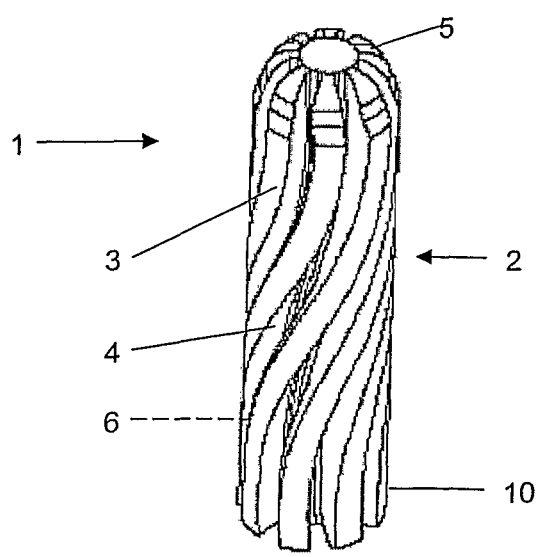

FIG. 1 (lateral view) and FIG. 2 (perspective view) are schematic illustrations of embodiments of a tampon according to the invention wherein the grooves and ribs are accentuated in order to better illustrate their path in the direction of the tampon body. The tampon representation in these figures corresponds to a pre-form of the tampon obtained after partial compression of a tampon blank in a pressing apparatus. This pre-form will undergo further radial compression in order to provide tampons having grooves which are substantially closed and a circumferential surface which is substantially smooth and soft, as illustrated in FIG. 5. The tampon 1 represented in FIGS. 1-2 has a longitudinal body 2 in an essentially cylindrical shape. The tampon is at least partially provided with longitudinal ribs 3 defined by longitudinal grooves 4. The tampon is provided with a round domed insertion end 5 and a withdrawal end (10). The tampon may be further provided with a withdrawal cord (not shown) at the withdrawal end in order to facilitate withdrawal of the tampon after use. In compressed condition, the longitudinal body 2 of tampon has a length L and a width W. For practical use (not illustrated) ribs 3 fit closely together near the circumferential surface, providing an essentially cylindrical and smooth surface. This facilitates handling of the tampon and makes insertion of the tampon more comfortable. On the tampon 1 an X,Y coordinate system can be represented, such that the Y axis divides the tampon in two halves in transversal direction and the X axis divides the tampon in two halves in axial direction.

The ribs 3 and the grooves 4 follow in the longitudinal direction of said tampon from the insertion end to the withdrawal end the path of a continuous curved line 6. The curved line shows a convex part 11 that is separated from a concave part 12 by a single point of inflection 13. The point of inflection 13 is substantially located in the middle part of the tampon longitudinal body, in an area covering the middle 50% of the tampon longitudinal body area (area indicated with A), and is in particular located on the X axis at a length L/2. The curve also shows two points 14, 15 which have a first derivative equal to zero. A first point 14 is located in an area covering the top 25% of the tampon longitudinal body area (area indicated with B). A second point 15 is located in an area covering the bottom 25% of the tampon longitudinal body area (area indicated with C).

Figure 3:
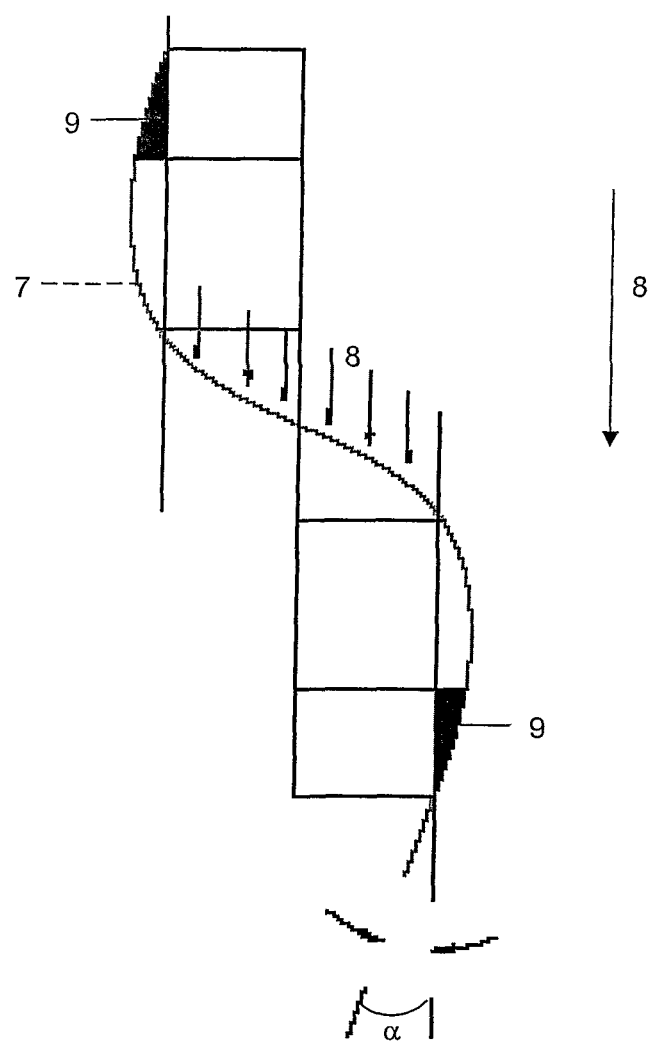

FIG. 3 schematically represents the sinusoidal path 7 of tampon grooves and tampon ribs of a prior art tampon. A problem associated with this type of grooved tampons, is that such tampons undergo substantial friction caused by the penetrating segments of pressing jaws when being released out of a pressing apparatus. The withdrawal direction of the tampon out of the apparatus is indicated by arrow 8. The black areas 9 indicate the regions of the tampon which undergo most friction, since in these regions the direction of the sinusoidal grooves is not in line with the release direction. The sinusoidal path of the grooves is curved inward, making an angle α between the release direction 8 of the tampon out of the press apparatus and the path followed by the grooves 7.

Figure 4:
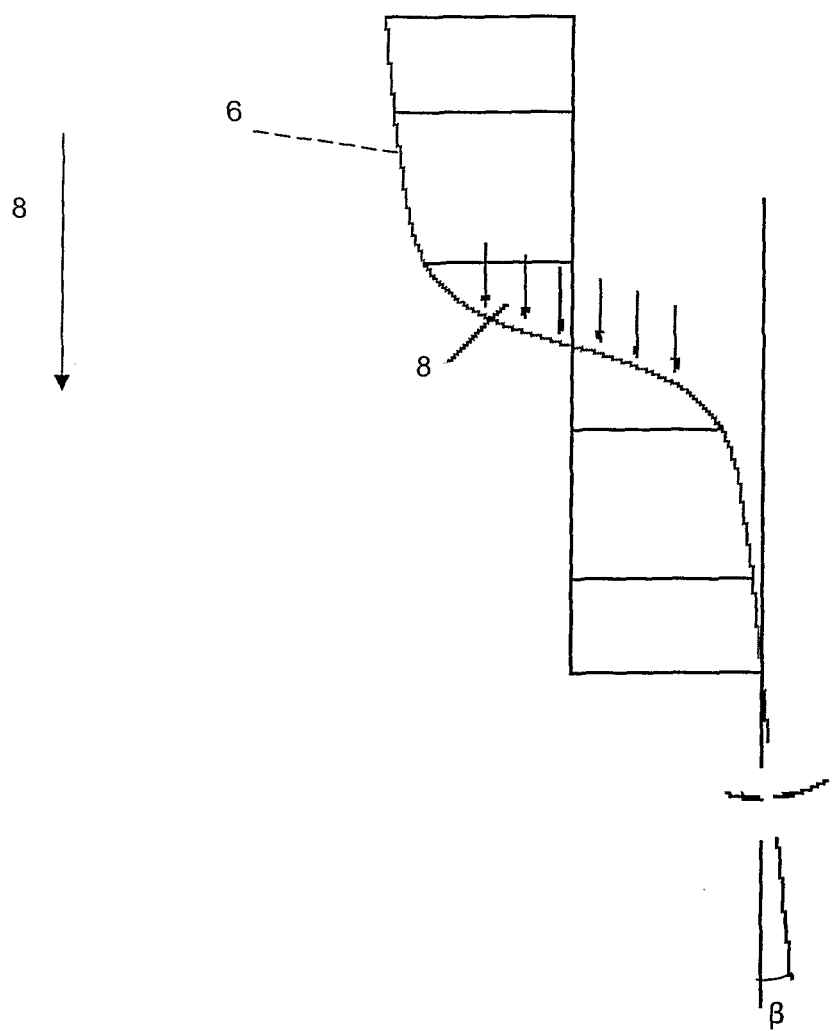
FIG. 4 schematically represents a path followed by grooves and ribs of a tampon according to the invention in the longitudinal (axial) direction Y of the tampon.
Figure 5A:
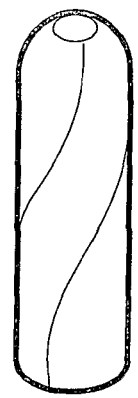
FIG. 5 A to C represents different embodiments of tampons according to the present invention showing 4, 6 and 8 grooves respectively.
Figure 5A:
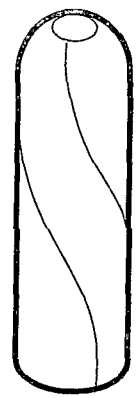
Figure 5B:
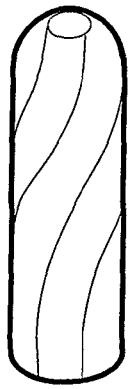
Figure 5B:
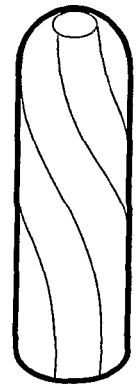
Figure 5C:
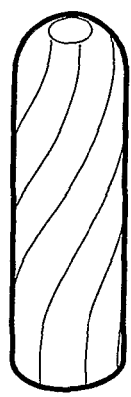
Figure 5C:
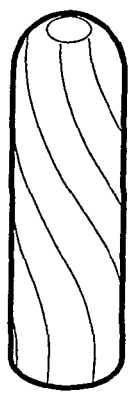

FIG. 4 schematically represents the curved path 6 of tampon grooves and tampon ribs of a tampon according to the present invention. The release direction out of the press is indicated by arrow 8. In such tampons friction between the grooves and the penetrating segments is considerably reduced when withdrawing the finished tampons out of the pressing apparatus, because the path of the grooves is substantially in line with the withdrawal direction of the tampons and curved outward under an angle β defining the angle that is formed between the release direction 8 of the tampon out of the press and the path followed by the grooves 6. As a result thereof, the release of a tampon as represented in FIG. 4 out of a pressing apparatus will be easier, will induce less friction between grooves and press apparatus, and thus will cause less damage to the grooves formed on the outer circumferential surface of the tampon, compared to the release of a tampon as represented in FIG. 3.

FIG. 5 are realistic illustrations of embodiments of a tampon according to the invention, obtained after radial compression of pre-formed tampons (such as those shown in FIGS. 1-2) in order to provide tampons having grooves which are substantially closed. In FIGS. 5A, 5B and 5C, tampons respectively having 4, 6 and 8 longitudinal grooves are represented. As can be seen on these figures, the side flanks of adjacent longitudinal ribs touch one another to form a soft, closed circumferential surface of the tampon. This circumferential surface of the tampon allows a gentler and therefore more pleasant introduction into and withdrawal from the body cavity. In accordance with the present invention the path of the grooves and ribs in the longitudinal direction of the tampon body between insertion and withdrawal part may go from convex to concave as shown in tampon representations in the left handed FIG. 5 A-C or from concave to convex, as shown in the right handed FIG. 5 A-C. It is however important to notice that each curve of the grooves in the represented tampon embodiments shows only one inflection point, and thus only one convex part and only one concave part.

The in FIG. 5 represented tampons are particularly preferred embodiments according to the present invention. The represented tampons show grooves and ribs which follow the path of a continuous curved line having only one point of inflection that is located about an imaginary transversal line on the tampon at length L/2. The curved line defining the path of the tampon grooves and ribs does not show any maximum or minimum point wherein the first derivative would be zero. In the unlikely event that such point would be present, it may be located in the top and/or the bottom compressed area of the tampon. From FIG. 5, it is clear that the path of the tampon grooves and ribs does not follow a periodic curve, and does not correspond to a wave function, since there is no cyclic returning pattern in the curve.

A tampon of the invention may optionally be provided with one or more markings on the surface. A marking may be provided by any mean means including printed using inks, or by impression. A marking may comprise any features including alpha numerals, graphic illustrations, patterns and/or photographic illustration. A marking may be, for example, information such as expiry date, absorbent capacity, use instruction, warning indications. Where a tampon is provided with information, it is an information carrier. A marking may also be advertising. A marking may provide product appeal to the user or groups of users. For example, it may comprise one or more images, patterns, graphics or alpha numerals designed to appeal s by way of aesthetic appearance and/or life-style association (e.g. cartoons, logos etc.).

A tampon of the invention may optionally be provided in one or more colors. Colors may be printed as mentioned above, or impregnated into the material. A color may indicate an expiry date, an absorbent capacity, a size or other information regarding the product. A color may be designed to appeal to a mind set of a user group by way of aesthetic appearance and/or life-style association.

It is a further aspect of the invention that a tampon is provided with a chemical indicator that is capable of indicative color change. Such indicator may show, for example, a medical condition. The chemical indicator may react within one or more agents in bodily fluids to indicate an abnormality. For example, a chemical indicator may change colour when a subject is suffering from a disease such as anaemia (by detecting iron/haemoglobin density), diabetes (by detecting glucose) or from the presence of sexually transmitted diseases (by detecting antigens towards for example, gonorrhea, syphilis, hepatitis A, B or C, herpes, HIV, chlamydia) etc . . . The indicator may also change color in accordance with the period in the menstrual cycle (by detecting hormones).

The invention further concerns a method for manufacturing the tampon of the invention. A strip of absorbent material having acceptable absorbency and modulus of elasticity properties that is capable of absorbing and/or retaining liquid, is wound up on itself to form an essentially cylindrical tampon blank.

In a preferred embodiment, the essentially cylindrical blank is at least partially surrounded by a covering. The covering is preferably not provided at the portion which will form the insertion end of the tampon. In order to improve the absorbing capacity and expansion capacity of the tampon, said covering is preferably a stretchable and/or elastic liquid-permeable covering.

The tampon can be provided with a withdrawal cord, according to any technique known in the art.

The tampons according to the present invention can be easily and rapidly manufactured by a process using a press apparatus showing press jaws with penetrating segments or cogs, such as for instance described in the European patent application having application number 03447303.3. Herein, the tampon blank is pressed with such pressing apparatus. In order to form the ribs of the tampon, the method comprises compressing the tampon blank on its outer circumferential surface, forming longitudinal grooves and a fibre core. Preferably, the fibre core has a higher degree of compression from which less compressed longitudinal ribs extend outwards. The degree of compression in the ribs is less than in tampons of the prior art, allowing the absorption of more liquid.

The process essentially comprising the steps of:
  inserting an essentially cylindrical blank of absorbing material in a press comprising press jaws including penetrating segments and pressing shoulders,
  pressing essentially radially the tampon blank in the press jaws, so that the penetrating segments penetrate the cylindrical blank to form ribs defined by grooves and the pressing shoulders press on the circumferential surface of the ribs so-formed,
  ejecting the so-formed pre-form,
  subjecting the pre-form to further radial pressure on its total circumference, so forming a tampon.

The manufacturing method is easy, rapid and cost-effective, since material loss can be significantly reduced.

In a preferred embodiment the method for producing a tampon according to the invention comprises the steps of:
  providing a tampon blank of fibrous material having a longitudinal axis;
  compressing in a press the tampon blank and forming longitudinal grooves at an outer circumferential surface of the tampon which follow the path in the longitudinal direction of said tampon of a continuous curved line, having only one point of inflection defining one convex part and one concave part, and
  withdrawing said pressed tampon out of the press in a longitudinal direction of the tampon body.

More in particular, in a preferred embodiment the method is as defined above, wherein said tampon blank is compressed in order to form longitudinal grooves at an outer circumferential surface of the tampon which follow the path in the longitudinal direction of said tampon of a curved line showing the function $$y = a\,x^m$$

wherein m is an odd positive whole number which is different from 1,
  wherein a is different from zero,
  wherein y corresponds to a value in the axial direction Y of the tampon body, and
  wherein x corresponds to a value in the transversal direction X of the tampon body.

In another preferred embodiment, the method is as defined above, wherein said tampon blank is compressed in order to form longitudinal grooves at an outer circumferential surface of the tampon which follow the path in the longitudinal direction of said tampon of a curved line showing a hyperbolic function or an inverse hyperbolic function.

In detail, a preferably cylindrical tampon blank is introduced in the press apparatus described above.

The tampon blank is radially compressed by press jaws, such as those described above. If the penetrating segments and the pressing shoulders are fixed to separate press jaws, the tampon blank may be first pressed with the penetrating segments and subsequently with the pressing shoulders. Alternatively, the penetrating segments and the pressing shoulders may press the tampon blank simultaneously. The latter will obviously be the case when the penetrating segments and pressing shoulders are fixed to the same press jaws. In the press, the tampon blank is preferably compressed in a single pressing operation by the penetrating segments and pressing shoulders simultaneously.

The penetrating segments will preferably press the tampon blank on strips of the circumferential surface that are narrower than the strips of the circumferential surface pressed by the pressing shoulders. Preferably also, the strips pressed by the penetrating segments have an equal length and width and the strips pressed by the pressing shoulders also have an equal length and width. In this way, ribs are formed, defined by longitudinal grooves on a solid fibre core. The pressing shoulders will press on the circumference of the so formed ribs in order to obtain an essentially cylindrical form with a smaller diameter. The memory effect of the tampon blank maintains the shape of the compressed tampon form.

The tampon blank, having been pressed by the penetrating segments and pressing shoulders, forms a pre-form, as for instance illustrated in FIGS. 1-2, which is ejected from the press. This pre-form is simultaneously subjected to final shaping downstream. This final shaping includes a radial pressure being exerted on the total circumference of the preform. This radial pressure has the effect that the adjacent longitudinal ribs are pressed against one another, so that the grooves are substantially closed and the circumferential surface of the tampon is substantially smooth and soft.

The tampon blank is, depending on the properties of the fibrous material used, in particular in the event of use of highly expansive fibers of irregular cross section with a strong memory effect, pressed at the temperature of the press jaws to the final shape of the tampon, in order to achieve the desired dimensional stability of the fibrous material by eliminating the memory effect of the fibers, which immediately becomes effective again on contact with bodily fluid and thus increases the expansion and absorption speed of the tampon with the least possible use of fibrous material, as illustrated in FIG. 5.

It is apparent that there has been provided in accordance with the invention, a tampon that fully satisfies the objects, aims, and advantages set forth above. While the invention has been described in conjunction with specific embodiments thereof, it is evident that many alternatives, modifications, and/or variations will be apparent to those skilled in the art in the light of the foregoing description. Accordingly, it is intended to embrace all such alternatives, modifications, and variations.

What is claimed is:

1. A tampon for feminine hygiene having a longitudinal body showing in compressed condition a length L and a width W, whereby said tampon comprises compressed absorbent fibrous material and has an outer circumferential surface which is provided with longitudinal grooves that are separated from each other by longitudinal ribs, wherein the path of said grooves and said ribs in the longitudinal direction of said tampon corresponds to a continuous curved line having only one point of inflection defining one convex part and one concave part wherein said curved line does not show a point having a first derivative equal to zero.

2. The tampon according to claim 1, wherein said point of inflection is substantially located in the middle part of the tampon longitudinal body.

3. The tampon according to claim 1, wherein said curved line is point symmetric in relation to said point of inflection.

4. The tampon according to claim 1, wherein the path of the grooves and the ribs in the longitudinal direction of said tampon corresponds to a curved line showing the function $$y = a\, x^m$$

wherein m is an odd positive whole number which is different from 1,
wherein a is different from zero,
wherein y corresponds to a value in the axial direction Y of the tampon body, and
wherein x corresponds to a value in the transversal direction X of the tampon body.

5. The tampon according to claim 1, wherein the path of the grooves and the ribs in the longitudinal direction of said tampon corresponds to a curved line showing the function $y=x^3$.

6. The tampon according to claim 1, wherein the path of the grooves and the ribs in the longitudinal direction of said tampon corresponds to a hyperbolic function, or an inverse hyperbolic function.

7. The tampon according to claim 6, wherein said function corresponds to any of the following functions:

$$y = \sin h\,(x),\ \text{or}$$

$$y = \tan h\,(x),\ \text{or}$$

$$y = \text{artan}\, h\,(x)$$

wherein y corresponds to a value in the axial direction Y of the tampon body, and
wherein x corresponds to a value in the transversal direction X of the tampon body.

8. The tampon according to claim 1, characterized by reference to a X,Y coordinate system represented on the tampon, such that the Y axis divides the tampon in two halves in transversal direction and the X axis divides the tampon in two halves in axial direction, x is between $-\tfrac{1}{2}$ W and $+\tfrac{1}{2}$ W.

9. The tampon according to claim 1 characterized by reference to a X,Y coordinate system represented on the tampon, such that the Y axis divides the tampon in two halves in transversal direction and the X axis divides the tampon in two halves in axial direction, y is between $-\tfrac{1}{2}$ L and $+\tfrac{1}{2}$ L.

10. The tampon according to claim 1, consisting essentially of a cylindrical shape comprising 3 to 12 longitudinal grooves.

11. The tampon according to claim 1, wherein the tampon comprises a dome shaped insertion end.

12. The tampon according to claim 1, wherein the tampon comprises a constricted withdrawal end.

13. The tampon according to claim 1, wherein said withdrawal end comprises a finger recess.

14. The tampon according to claim 1, comprising a withdrawal cord which extends from said withdrawal end.

15. The tampon according to claim 1, wherein the tampon comprises a fiber core of highly compressed fibrous material and an outer circumferential surface comprising longitudinal ribs that extend radially outwards and that are defined by said longitudinal grooves.

16. The tampon according to claim 1, wherein said longitudinal ribs are at least partially relatively uncompressed compared with the fiber core.

17. The tampon according to claim 1, comprising one or more markings on the surface.

18. A method for producing a tampon according to claim 1, comprising the steps of:
providing a tampon blank of fibrous material having a longitudinal axis;
compressing in a press the tampon blank and forming longitudinal grooves at an outer circumferential surface of the tampon which follow the path in the longitudinal direction of said tampon of a continuous curved line having only one point of inflection defining one convex part and one concave part, wherein said curved line does not show a point having a first derivative equal to zero, and
withdrawing said pressed tampon out of the press in a longitudinal direction of the tampon body.

19. The method according to claim 18, wherein said tampon blank is compressed in order to form longitudinal grooves at an outer circumferential surface of the tampon which follow the path in the longitudinal direction of said tampon of a curved line showing the function $$y = a\, x^m$$

wherein m is an odd positive whole number which is different from 1,
wherein a is different from zero,
wherein y corresponds to a value in the axial direction Y of the tampon body, and
wherein x corresponds to a value in the transversal direction X of the tampon body.

20. The method according to claim 18, wherein said tampon blank is compressed in order to form longitudinal grooves at an outer circumferential surface of the tampon which follow the path in the longitudinal direction of said tampon of a curved line showing a hyperbolic function or an inverse hyperbolic function.

21. A press suitable for manufacturing of a tampon according to claim 1 by pressing absorbing fibrous material radially, comprising press jaws including penetrating segments for pressing the absorbing material radially and pressing shoulders, said penetrating segments essentially having a shape of a continuous curved line havin onl one point of inflection defining one convex part and one concave part, wherein said curved line does not show a point having a first derivative equal to zero.

22. The tampon according to claim 2, wherein said point of inflection is in an area covering the middle 50% of the tampon longitudinal body area.

23. The tampon according to claim 22, wherein said point of inflection is located about an imaginary transversal line on the tampon at length L/2.

* * * * *

UNITED STATES PATENT AND TRADEMARK OFFICE
CERTIFICATE OF CORRECTION

PATENT NO.       : 8,864,732 B2
APPLICATION NO.  : 11/813970
DATED            : October 21, 2014
INVENTOR(S)      : Werner Van Ingelgem et al.

It is certified that error appears in the above-identified patent and that said Letters Patent is hereby corrected as shown below:

In the Specification

In column 2 at line 34, Change "ore" to --or--.

In column 3 at line 13, Change "pad"" to --part"--.

In column 4 at line 67, Change "body" to --body.--.

In column 6 at line 27 (approx.), Change "-½, L." to -- -½ L,--.

In column 7 at line 13, Change "sin h" to --sinh--.

In column 7 at line 13, Change "tan h" to --tanh--.

In column 7 at line 16, Change "sin h" to --sinh--.

In column 7 at lines 17-18, Change "sin h" to --sinh--.

In column 7 at line 18, Change "tan h" to --tanh--.

In column 7 at line 20, Change "sin h" to --sinh--.

In column 7 at line 20, Change "cos h" to --cosh--.

In column 7 at line 20, Change "sin h" to --sinh--.

In column 7 at lines 20-21, Change "cos h" to --cosh--.

In column 7 at line 23, Change "artan h" to --artanh--.

In column 7 at line 27, Change "artan h" to --artanh--.

In the Claims

In column 14 at line 29 (approx.), In Claim 7, change "sin h" to --sinh--.

In column 14 at line 31 (approx.), In Claim 7, change "tan h" to --tanh--.

In column 14 at line 34 (approx.), In Claim 7, change "artan h" to --artanh--.

In column 16 at line 16, In Claim 21, change "havin onl" to --having only--.

Signed and Sealed this
Twenty-sixth Day of May, 2015

Michelle K. Lee
*Director of the United States Patent and Trademark Office*